United States Patent [19]

Wiezer et al.

[11] 4,104,251
[45] Aug. 1, 1978

[54] SUBSTITUTED TETRAALKYLPIPERIDONE-4-OXIMES

[75] Inventors: Hartmut Wiezer, Gersthofen; Gerhard Pfahler, Augsburg; Norbert Mayer, Gersthofen, all of Fed. Rep. of Germany

[73] Assignee: Hoechst Aktiengesellschaft, Frankfurt am Main, Fed. Rep. of Germany

[21] Appl. No.: 742,233

[22] Filed: Nov. 16, 1976

[30] Foreign Application Priority Data

Nov. 21, 1975 [DE] Fed. Rep. of Germany ....... 2552176

[51] Int. Cl.$^2$ .................... C08K 5/34; C07D 211/72
[52] U.S. Cl. ..................... 260/45.8 N; 260/293.62; 260/293.63; 260/293.64; 260/293.73; 260/293.77; 260/293.85; 260/293.86
[58] Field of Search ................. 260/293.62, 293.63, 260/293.64, 293.73, 293.77, 293.85, 293.86, 45.8 N

[56] References Cited

U.S. PATENT DOCUMENTS

| 3,780,178 | 12/1973 | Tetenbaum ............... 260/293.85 |
| 4,033,928 | 7/1977 | Randell et al. ............. 260/45.8 N |

Primary Examiner—Natalie Trousof
Assistant Examiner—Bernard Dentz
Attorney, Agent, or Firm—Connolly and Hutz

[57] ABSTRACT

Novel derivatives of 2,2,6,6-tetraalkylpiperidone-4-oximes constitute excellent stabilizers for synthetic polymer compositions against the action of ultraviolet radiation and heat. The compounds can be used either per se or in admixture with known stabilizers.

6 Claims, No Drawings

SUBSTITUTED TETRAALKYLPIPERIDONE-4-OXIMES

This invention relates to derivatives of 2,2,6,6-tetraalkyl-piperidone-4-oximes, which can be used as stabilizers for organic materials.

The substituted tetraalkylpiperidone-4-oximes according to the invention are compounds of the formula I

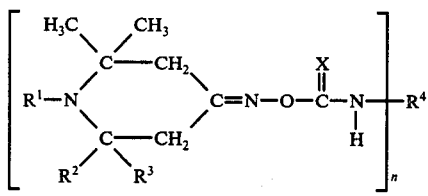

in which
$n$ is 1 or 2,
$R^1$ represents hydrogen or oxygen or a hydroxyl group, preferably hydrogen,
$R^2$ and $R^3$ represent identical or different linear or branched, but not in α-position, alkyl radicals having from 1 to 9, preferably from 1 to 4 carbon atoms, or a cycloalkyl radical having from 5 to 7 carbon atoms and including the carbon atom of the ring,
$R^4$ represents, when $n$ is equal to 1, a linear, cyclic or branched alkyl radical having from 1 to 18, preferably from 1 to 6 carbon atoms or an aryl radical having from 6 to 10 carbon atoms and being optionally substituted by a halogen atom, preferably a chlorine atom, or an alkyl or alkoxy radical each having from 1 to 4 carbon atoms, or when $n$ is equal to 2, an alkylene radical having from 1 to 6 carbon atoms or an arylene radical optionally substituted by an alkyl radical having from 1 to 4 carbon atoms, and
X stands for oxygen or sulfur.

Especially valuable substances are compounds of formula I a

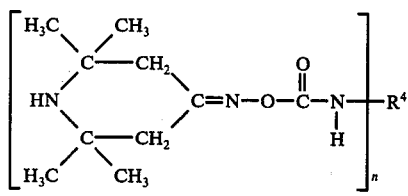

in which
$n$ is 1 or 2 and
$R^4$ represents, when $n$ is equal to 1, a linear alkyl radical having from 1 to 6 carbon atoms, a branched alkyl radical having from 3 to 6 carbon atoms, a cycloalkyl radical having 5, 6 or 7 carbon atoms, or an aryl radical having 6 or 10 carbon atoms which may be substituted by a chlorine atom, or when $n$ is equal to 2, a linear alkylene radical having from 1 to 6 carbon atoms.

The following compounds are, for example, representatives of the 2,2,6,6-tetraalkylpiperidone-4-oxime derivatives of the invention.

2,2,6,6-tetralmethyl-4-(butylcarbamoyloximino)-piperidine,
2,2,6,6-tetramethyl-4-(tert.-butylcarbamoyloximino)-piperidine,
2,2,6,6-tetramethyl-4-(cyclohexylcarbamoyloximino)-piperidine,
2,2,6,6-tetramethyl-4-(phenylcarbamoyloximino)-piperidine,
2,2,6,6-tetramethyl-4-(m-chlorphenylcarbamoyloximino)-piperidine,
2,2,6,6-tetramethyl-4-(p-chlorphenylcarbamoyloximino)-piperidine,
2,2,6,6-tetramethyl-4-(naphthyl-1-carbamoyloximino)-piperidine,
1,6-bis(2,2,6,6-tetramethyl-4-carbamoyloxyiminopiperidino-4-)hexane The compounds according to the invention are prepared by reacting an isocyanate or isothiocyanate of the formula II

in which $R^4$, X and $n$ have the same meaning as in Formula I with a piperidone-oxime of the formula III

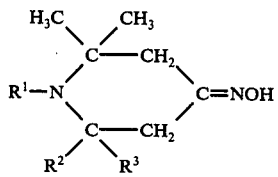

in which $R^1$, $R^2$ and $R^3$ have the same meanings as in formula I.

Suitable compounds of formula II are mono- and diisocyanates and mono- and diisothiocyanates, such as for example methyl, ethyl, propyl, butyl, isobutyl, tert-butyl, stearyl, cyclohexyl, and phenyl isocyanate or isothiocyanate. There can also be used halogenophenyl, alkylphenyl, alkoxyphenyl and naphthyl compounds in which the halogen is preferably chlorine and bromine and the alkyl radicals have from 1 to 4 carbon atoms. Suitable diisocyanates or diisothiocyanates are, for example, hexamethylene and toluylene diisocyanate and hexamethylene and toluylene diisothiocyanate.

The piperidone-oximes of formula III are preferably those in which $R^1$ represents hydrogen and $R^2$ and $R^3$ represent methyl groups, such as for example 2,2,6,6-tetramethyl-piperidone-4-oxime, 1-hydroxy-2,2,6,6-tetramethyl-piperidone-4-oxime and 1-hydroxy-2,2,6,6-tetramethyl-piperidone-4-oxime.

To prepare the 2,2,6,6-tetralkyl-piperidone-4-oxime derivatives the stoichiometrically required amount of isocyanate or isothiocyanate II is added dropwise at a temperature of from 0° to 100°, preferably 20° to 60° C, to the compound III in a solvent inert with respect to isocyanate or isothiocyanate, the solvent is distilled off and the remaining product is purified, if necessary, for example by recrystallization. Suitable solvents, which are used in 1 to 10 times the amount by weight, calculated on the reaction components, are ethers, hydrocarbons, chlorinated hydrocarbons, or aromatic hydrocarbons.

The 2,2,6,6-tetraalkylpiperidone-4-oxime derivatives of the invention confer upon synthetic polymer compositions an outstanding stability to decomposition by the action of ultraviolet radiation or heat. The color properties of the synthetic polymer compositions are not effected by the presence of the novel compounds.

Synthetic polymer compositions which can be protected against the detrimental effect of light and heat are polyolefins, including polyisoprene, polybutadiene, polystyrene, polypropylene, and polyethylene of low and high density, other olefin polymers and ethylene-propylene copolymers, ethylene-butene copolymers, ethylene-vinyl acetate copolymers, styrene-butadiene copolymers, acrylonitrile-styrene-butadiene copolymers, other copolymers of further ethylenically unsaturated monomers and olefins. The term polymer compositions is also intended to include homopolymers of vinyl chloride and vinylidene chloride, copolymers of vinyl chloride and vinylidene chloride, copolymers of vinyl chloride or vinylidene chloride with vinyl acetate or other olefinically unsaturated monomers, polyacetals, polyesters, for example polyethylene terephthalate, polyamides, for example nylon 6, nylon 6,6 and nylon 6,10, polyurethane and epoxide resins.

The amount of stablizers to be added to the synthetic polymers can considerably vary, depending on the type, the properties and the purpose of application of the respective polymer. In general 0.01 to 5, preferably 0.1 to 3 and more preferably 0.5 to 3% by weight of stabilizers, calculated on the amount of the synthetic polymer are used. The compounds of the invention can be added either singly or in the form of mixtures of several compounds.

The compounds are incorporated into the synthetic polymers by known methods. The stabilizers can be mixed with the synthetic polymer in the form of a dry powder or a solution, suspension or emulsion of the stabilizer is blended with a solution, suspension or emulsion of the synthetic polymer. The stabiliziers of the invention are effective per se as well as in admixture with the usual light stabilizers (UV stabilizers and quenchers) or heat stabilizers on the basis of phenolic, sulfidic or phosphorus-containing antioxidants.

The usual stabilizers are, more particularly, for example 2,6-di-tert-butyl-p-cresol, 3,5-di-tert-butyl-4-hydroxyphenyl propioic acid ester, alkylidene-bis-alkylphenols, thiodipropionic acid esters of fatty alcohols, as well as dioctadecyl sulfide and disulfide. Suitable phosphorus-containing compounds are, for example, trisnonylphenyl phosphite, distearylpentaerythrityl diphosphite and esters of pentaerythrityl phospite. Examples of UV absorbers are benzotriazole compounds, such as 2-(2'-hydroxy-5'-methylphenyl)-benzotriazole, and of quenchers recently proposed piperidone stabilizers as well as metal chelates.

An effective stabilizer combination for halogen-free poly-α-olefins, for example high, medium and low pressure polymers of $C_2$ to $C_4$ α-olefins, especially polyethylene and polypropylene, or copolymers of such α-olefine, consists, for example, of 0.1 to 3 parts by weight of a compound according to the invention, 0.05 to 3 parts by weight of a phenolic stabilizer and optionally 0.1 to 3 parts by weight of a phosphite and/or 0.01 to 3 parts by weight of a UV stabilizer of the group of alkoxyhydroxybenzophenones, hydroxyphenyl benzotriazoles, salicyclic acid phenyl esters, benzoic acid hydroxyphenyl ester, benzylidene malonic acid mononitrile esters, so-called quenchers such as nickel chelates, hexamethyl phosphoric acid triamide, or representatives of the group of hindered amine light stabilizers which have recently become known.

In the stabilization of chlorine-containing vinyl homo- and co-polymers, for example polyvinyl chloride, polyvinylidene chloride, polyvinyl chloracetate, vinyl chloride-α-olefin copolymers and chlorinated polyolefins, such as chlorinated polyethylene and chlorinated polypropylene, the addition of the novel stabilizers, in addition to known stabilizers such as metal compounds, epoxide stabilizers, phosphites and optionally polyhydric alcohols, further improves the heat and light stability.

Metal compounds known as stabilizers are, for example, calcium, barium, strontium, zinc, cadmium, magnesium, aluminum, and lead soaps of aliphatic carboxylic acids or hydroxycarboxylic acids having from 12 to 32 carbon atoms, salts of the said metals with aromatic carboxylic acids, for example benzoates or salicylates, (alkyl)-phenolates of the aforesaid metals, organotin compounds, for example dialkyltin thioglycolates and carboxylates.

Known epoxide stabilizers are, for example, epoxidized higher fatty acids such as epoxidized soybean oil, tall oil, linseed oil, or epoxidized butyl oleate and epoxides of long chain α-olefins.

Suitable phosphites are trisnonylphenyl phospite, trislauryl phosphite or esters of pentaerythritol phosphite.

Polyhydric alcohols are intended to include, for example, pentaerythritol, trimethylolpropane, sorbitol, or mannitol, i.e. preferably alcohols having 5 to 6 carbon atoms and from 3 to 6 hydroxyl groups.

A stabilizer combination for the stabilization of halogen-containing polymers consists, for example, of 0.1 to 10 parts by weight of metal compounds known as stabilizers, 0.1 to 10 parts by weight of a known epoxide stabilizer, 0.05 to 5 parts by weight of a phosphite, 0.1 to 1 part by weight of a polyhydric alcohol and 0.01 to 5 parts by weight of a compound of the invention, calculated on 100 parts by weight of polymer.

The folowing examples illustrate the invention.

EXAMPLE 1

2,2,6,6-tetramethyl-4-butylcarbamoyl-oximinopiperidine

A solution of 9.9 grams of n-butyl isocyanate in 25 ml of toluene was added dropwise, while stirring at 40° to 50° C, to a solution of 17 grams of 2,2,6,6-tetramethyl-piperidone-4-oxime in 100 ml of toluene purified over sodium. Stirring of the mixture was continued for ½ hours, the toluene was removed, the residue was finely ground with petroleum ether and the crystalline residue was recrystallized from n-heptane. 19 grams of white crystals were obtained having a melting point of 58° to 60° C.

IR spectrum (pressed structure) $v_{C=N}$ 1635 cm$^{-1}$, $v_{C=O}$ 1722 cm$^{-1}$ Analytical data for $C_{14}H_{27}N_3O_2$: calculated C, 62.5%; H, 10.1%; N, 15.6%. found: C, 62.2%; H, 10.3%; N, 15.3%.

EXAMPLE 2

2,2,6,6-tetramethyl-4-tert-butylcarbamoyl-oximinopiperidine

The reaction was carried out as descirbed in Example 1. In the stead of n-butyl isocyanate tert-butyl isocyanate was used. Yield: 20 grams of white crystals; melting point 136° – 139° C.

IR spectrum (pressed piece): $\nu_{C=N}$1635 cm$^{-1}$, $\nu_{C=O}$1725 cm$^{-1}$ Analytical data for $C_{14}H_{27}N_3O_2$: calculated: C, 62.5%; H, 10.1%; N, 15.6%. found: C, 62.4%; H, 10.2%; N, 15.2%.

EXAMPLE 3

2,2,6,6-tetramethyl-4-cyclohexylcarbamoyl-oximinopiperidine

Under the conditions specified in Example 1 the piperidone 4-oxime was reacted with 12.5 grams of cyclohexyl isocyanate.

Yield 24 grams; melting point 105° to 107° C

IR spectrum (pressed piece) $\nu_{C=N}$1635 cm$^{-1}$, $\nu_{C=O}$1725 cm$^{-1}$ Analytical data for $C_{16}H_{29}N_3O_2$: calculated C, 65.0%; H, 9.9%; N, 14.2%. found: C, 65.5%; H, 10.1%; N, 14.0%.

EXAMPLE 4

2,2,6,6-tetramethyl-4-phenylcarbamoyl-oximinopiperidine

Under the conditions specified in Example 1 the piperidone 4-oxime was reacted with 11.9 grams of phenyl isocyanate.

Yield; 25 grams, melting point 112° C

IR spectrum (pressed piece) $\nu_{C=N}$1644 cm$^{-1}$, $\nu_{C=O}$1715 cm$^{-1}$ Analytical data for $C_{16}H_{23}N_3O_2$: calculated: C, 66.4%; H, 7.7%; N, 14.5%. found: C, 66.4%; H, 8.0%; N, 14.2%.

EXAMPLE 5

2,2,6,6-tetramethyl-4-chlorophenylcarbamoyl-oximinopiperidine

The reaction was carried out under the conditions specified in Example 1 using 15.4 grams of m-chlorophenyl isocyanate.

Yield: 32 grams; melting point 121° to 123° C.

IR spectrum (pressed piece): $\nu_{C=N}$1635 cm$^{-1}$, $\nu_{C=O}$1715 cm$^{-1}$ Analytical data for $C_{16}H_{22}ClN_3O_2$: calculated: C, 59.4%; H, 6.8%; N, 12.9%. found: C, 59.8%; H, 6.9%; N, 12.6%.

EXAMPLE 6

2,2,6,6-tetramethyl-4-p-chlorophenylcarbamoyl-oximinopiperidine

The reaction was carried out as described in Example 1, but with the use of 15.4 grams of p-chlorophenyl isocyanate.

Yield: 27 grams; melting point 98° to 100° C

IR spectrum (pressed piece) $\nu_{C=N}$1643 cm$^{-1}$, $\nu_{C=O}$1715 cm$^{-1}$ Analytical data for $C_{16}H_{22}ClN_3O_2$: calculated: C, 59.4% H, 6.8%; N, 12.9%. found: C, 59.6%; H, 7.1%; N, 12.6%.

EXAMPLE 7

2,2,6,6-tetramethyl-4-naphthylcarbamoyl-oximinopiperidine

The reaction was carried out as described in Example 1 with the exception that 16.9 grams of naphthyl isocyanate-1 were used instead of butyl isocyanate.

Yield: 25 grams; melting point 103° to 105° C.

IR spectrum (pressed piece): $\nu_{C=N}$1650 cm$^{-1}$, $\nu_{C=O}$1735 cm$^{-1}$ Analytical data for $C_{20}H_{25}N_3O_2$: calculated: C, 70.8%; H, 7.4%; N, 12.4%. found: C, 71.7%; H, 7.7%; N, 12.4%.

EXAMPLE 8

1,6-bis(2,2,6,6-tetramethyl-4-carbamoyl-oximinopiperidino-4)-hexane

The compound was prepared under the conditions of Example 1 with the exception that 8.4 grams of hexamethylene diisocyanate were used instead of butyl isocyanate.

Yield: 22 grams; melting point 117° to 119° C

IR spectrum (pressed piece): $\nu_{C=N}$1640 cm$^{-1}$, $\nu_{C=O}$1695–1725 cm$^{-1}$ Analytical data for $C_{26}H_{48}N_6O_4$: calculated: C, 61.4%; H, 9.5%, N, 16.4%. found: C, 61.4%; H, 9.9%; N, 16.4%.

EXAMPLE 9

This example is intended to illustrate the light stabilizing effect of some of the compounds of the invention when used in a poly-α-olefin.

100 parts by weight of polypropylene having a melt index $i_5$ of about 6 grams per 20 minutes (measured analogous to ASTM D 1238–62 T) and a density of 0.96 g/cc were mixed with 0.10 part by weight of a bis(4'-hydroxy-3'-tert-butylphenyl)butanoic acid ester 0.15 part by weight of laurin thiodipropionic acid ester 0.20 part by weight of calcium stearate and 0.30 part by weight of the stabilizer according to the invention to be tested and the mixture was homogenized for 5 minutes at 200° C on a two roller mill. The molten plastics composition was then molded at 200° C into a sheet having a thickness of 1 mm. When the sheet had cooled down test specimens were punched out according to DIN 53 455.

To measure the stability of light the test specimens were subjected to the alternating light of a weathering apparatus (Xenotest 150 of Messrs. Hanau Quarzlampen GmbH). The intensity of radiation was modulated through 6 IR windows and 1 UV window (DIN 53 387). The time of exposure in hours (endurance) was measured after which the absolute elongation at break had dropped to 10%. The elongate at break was determined on a tensile tester of Messrs. Instron at a draw-off rate of 5 m/min.

The results are listed in the following table.

| stabilizer of invention according to Example | time of exposure (Hours) |
|---|---|
| without | 560 |
| 3 | 1 000 |
| 6 | 1 000 |
| 8 | 1 000 |

What is claimed is:
1. A compound of the formula

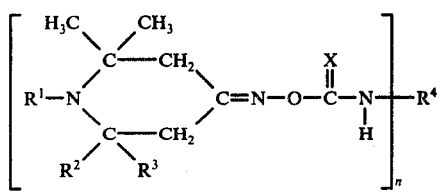

in which
 $n$ is 1 or 2,
 $R^1$ represents hydrogen or oxygen or a hydroxyl group,
 $R^2$ and $R^3$ represent identical or different linear or branched, but not in alpha-position, alkyl radicals having from 1 to 9 carbon atoms or $R^2$ and $R^3$ form a cycloalkyl ring having 5 to 7 carbon atoms inclusive of the carbon atom of the hetero ring,
 $R^4$ represents, when $n$ is equal to 1, a linear, cyclic or branched alkyl radical having from 1 to 18 carbon atoms or a phenyl- or naphthyl radical unsubstituted or substituted by a halogen atom or an alkyl or alkoxy radical each having from 1 to 4 carbon atoms, or, when $n$ is equal to 2, an alkylene radical having from 1 to 6 carbon atoms or a phenylene or naphthalene radical unsubstituted or substituted by an alkyl radical having from 1 to 4 carbon atoms, and
 X stands for oxygen or sulfur.

2. A compound of the formula

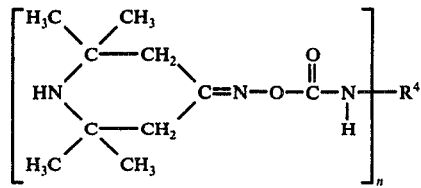

in which
 $n$ is 1 or 2 and
 $R^4$ represents, when $n$ is equal to 1, a linear alkyl radical having from 1 to 6 carbon atoms, a branched alkyl radical having from 3 to 6 carbon atoms, a cycloalkyl radical having 5, 6, or 7 carbon atoms, or an aryl radical having 6 or 10 carbon atoms unsubstituted or substituted by a chlorine atom, or,
 when $n$ is equal to 2, a linear alkylene radical having from 1 to 6 carbon atoms.

3. A compound of claim 1 wherein $R^1$ is hydrogen.

4. A process for stabilizing synthetic polymers against the detrimental effect of light and heat, which comprises adding to the polymers during processing from 0.01 to 5% by weight, calculated on the polymer, of a compound as claimed in claim 1.

5. A process of claim 4 wherein other stabilizing compounds in addition to a compound of claim 1 are added to the polymers during processing.

6. Stabilized synthetic polymer compositions containing as stabilizer a compound as claimed in claim 1 in an amount of from 0.01 to 5% by weight calculated on the polymer.

* * * * *